United States Patent
Smits et al.

(10) Patent No.: US 10,687,875 B2
(45) Date of Patent: Jun. 23, 2020

(54) RIB RECONSTRUCTION DEVICE

(71) Applicant: Biomet Manufacturing, LLC, Warsaw, IN (US)

(72) Inventors: Aaron Smits, Fort Wayne, IN (US); Brett Baver, West Chester, OH (US); Megan Courtney, Plover, WI (US)

(73) Assignee: Biomet Manufacturing, LLC, Warsaw, IN (US)

( * ) Notice: Subject to any disclaimer, the term of this patent is extended or adjusted under 35 U.S.C. 154(b) by 222 days.

(21) Appl. No.: 15/548,174

(22) PCT Filed: Feb. 13, 2015

(86) PCT No.: PCT/US2015/015904
§ 371 (c)(1),
(2) Date: Aug. 2, 2017

(87) PCT Pub. No.: WO2016/130154
PCT Pub. Date: Aug. 18, 2016

(65) Prior Publication Data
US 2018/0021074 A1  Jan. 25, 2018

(51) Int. Cl.
*A61B 17/80* (2006.01)
*A61B 17/70* (2006.01)
(Continued)

(52) U.S. Cl.
CPC ...... *A61B 17/8076* (2013.01); *A61B 17/7053* (2013.01); *A61B 17/823* (2013.01); *A61B 17/8685* (2013.01); *A61B 2017/568* (2013.01)

(58) Field of Classification Search
CPC .......................... A61B 17/80; A61B 17/8076
See application file for complete search history.

(56) References Cited

U.S. PATENT DOCUMENTS 4,327,715 A   5/1982   Corvisier
5,261,908 A   11/1993  Campbell, Jr.
(Continued)

FOREIGN PATENT DOCUMENTS

CN   2061042 U    8/1990
CN   102170923 A   8/2011
(Continued)

OTHER PUBLICATIONS

"International Application Serial No. PCT/US2015/015904, International Preliminary Report on Patentability dated Aug. 24, 2017", 11 pgs.
(Continued)

*Primary Examiner* — Christopher J Beccia
(74) *Attorney, Agent, or Firm* — Schwegman Lundberg & Woessner, P.A.

(57) ABSTRACT

An apparatus (10) for the correction of chest deformities is provided and includes a rib implant (26) for mounting to a rib, a sternal implant (22) for mounting to a sternum, and a first elongate member (24). The rib implant includes a first aperture (44) having a first axis (45). The sternal implant includes a second aperture (140) having a second axis (143). The first elongate member has a first end (152) adjustably received in the first aperture and a second end (150) adjustably received in the second aperture.

20 Claims, 7 Drawing Sheets

(51) Int. Cl.
*A61B 17/82* (2006.01)
*A61B 17/56* (2006.01)
*A61B 17/86* (2006.01)

(56) References Cited

U.S. PATENT DOCUMENTS

| | | | |
|---|---|---|---|
| 8,597,327 B2 * | 12/2013 | Stone | A61B 17/0401 |
| | | | 606/228 |
| 2004/0117016 A1 | 6/2004 | Abramson | |
| 2008/0234742 A1 | 9/2008 | Cascarino | |
| 2010/0004697 A1 * | 1/2010 | Fortin | A61B 17/66 |
| | | | 606/86 R |
| 2011/0251540 A1 | 10/2011 | Notrica | |
| 2013/0197521 A1 * | 8/2013 | Seykora | A61B 17/8076 |
| | | | 606/75 |
| 2014/0135853 A1 * | 5/2014 | Reisberg | A61B 17/8076 |
| | | | 606/324 |
| 2015/0119887 A1 * | 4/2015 | May | A61B 17/15 |
| | | | 606/71 |

FOREIGN PATENT DOCUMENTS

| | | |
|---|---|---|
| CN | 103767778 A | 5/2014 |
| CN | 107427318 | 12/2017 |
| FR | 3004337 A1 | 10/2014 |
| JP | 0690962 A | 4/1994 |
| JP | H0680412 U | 11/1994 |
| JP | 5042689 B2 | 7/2012 |
| JP | 2013517875 A | 5/2013 |
| JP | 6454023 B2 | 12/2018 |
| WO | WO-2004028412 A1 | 4/2004 |
| WO | WO-2014144479 A1 | 9/2014 |
| WO | WO-2016130154 A1 | 8/2016 |

OTHER PUBLICATIONS

"European Application Serial No. 15706135.9, Response filed Apr. 3, 2018 to Office Action dated Sep. 22, 2017", 10 pgs.
"Chinese Application Serial No. 201580078047.2, Office Action dated Jul. 3, 2019", W/English Translation, 8 pgs.
"International Application Serial No. PCT/US2015/015904, International Search Report dated Oct. 23, 2015", 4 pgs.
"International Application Serial No. PCT/US2015/015904, Written Opinion dated Oct. 23, 2015", 9 pgs.
"Australian Application Serial No. 2015382434, First Examination Report dated Sep. 19, 2019", 3 pgs.
"Chinese Application Serial No. 201580078047.2, Response filed Jan. 8, 2020 to Office Action dated Jul. 3, 2019", w/ English Claims, 15 pgs.

* cited by examiner

RIB RECONSTRUCTION DEVICE

CLAIM OF PRIORITY

This patent application is a U.S. National Stage Filing under 35 U.S.C. 371 from International Patent Application Serial No. PCT/US2015/015904, filed. Feb. 13, 2015, published on Aug. 18, 2016 as WO2016/130154 A1, the content of which is incorporated herein by reference in its entirety.

FIELD

The present disclosure relates to a rib reconstruction device or assembly, and more particularly to a system for correcting abnormalities in a thoracic cavity, including defects in rib cage.

BACKGROUND

This section provides background information related to the present disclosure and is not necessarily prior art.

Defects, injuries and abnormalities in the thoracic cavity, including defects associated with the rib cage, chest wall, and sternum, can cause several problems and lead to long term complications. For example, defects in the thoracic cavity can restrict lung capacity and lead to difficulty breathing. Moreover, thoracic cavity defects leave many of the body's vital organs (e.g., lungs, heart, liver, etc.) susceptible to traumatic injury. These defects can arise from congenital deformities (e.g., pectus excavatum or hollow chest, Poland syndrome, fused ribs, etc.) or disease (e.g., cancer). In some cases, surgery may be required to correct the defects in the thoracic cavity. Known surgical techniques often use metal reconstructive devices or implants. The reconstructive devices are often fixed to existing tissue or bone, and focus primarily on small, localized defects in the thoracic cavity. In this regard, it may be desirable to provide a surgical system and method that allows a user to repair variously sized defects in the thoracic cavity, and/or repair the defects when the amount of available tissue and/or bone is limited.

SUMMARY

This section provides a general summary of the disclosure, and is not a comprehensive disclosure of its full scope or all of its features.

In one configuration, the present disclosure provides an apparatus for the correction of chest deformities. The apparatus includes a rib implant for mounting to a rib, a sternal implant for mounting to a sternum, and a first elongate member. The rib implant includes a first aperture having a first axis. The sternal implant includes a second aperture having a second axis. The first elongate member has a first end adjustably received in the first aperture and a second end adjustably received in the second aperture.

In some configurations, the first axis is generally parallel to the second axis.

In some configurations, the first axis is generally aligned with the second axis.

In some configurations, the rib implant includes a third aperture having a third axis, and the rib is adjustably received in the third aperture.

In some configurations, the third axis intersects the first axis.

In some configurations, the third axis is generally parallel to the first axis.

In some configurations, the rib implant includes a first channel configured to receive a first rib, the first channel including a third axis intersecting the second axis.

In some configurations, the apparatus includes a suture member operatively securing the first rib within the first channel.

In some configurations, the apparatus includes a plate member for clamping the rib between the plate member and the rib implant.

In some configurations, the apparatus includes a second rib implant for mounting to a rib. The second rib implant can include a third aperture having a third axis. The sternal implant can include a fourth aperture having a fourth axis. A second elongate member can include a first end adjustably received in the third aperture and a second end adjustably received in the fourth aperture.

In some configurations, the third and fourth axes are generally parallel to the first and second axes.

In some configurations, the first rib implant includes a fifth aperture having a fifth axis, and the second rib implant includes a sixth aperture having a sixth axis.

In some configurations, the fifth axis is generally parallel to the sixth axis and generally perpendicular to the third and fourth axis.

In some configurations, the support member is disposed in the fifth and sixth apertures.

In some configurations, the first elongate member is flexible.

In another configuration, the present disclosure provides an apparatus for the correction of chest deformities. The apparatus includes a first bracket for mounting to a first rib, a second bracket for mounting to a second rib, a plate, and a sternal implant. The first bracket mounts to a first rib and includes a first rib-receiving aperture, a first rod-receiving aperture, and a first support member-receiving aperture. The first rib-receiving aperture includes a first rib-receiving axis. The first rod-receiving aperture includes a first rod-receiving axis generally perpendicular to the first rib-receiving axis. The first support member-receiving aperture includes a first support member-receiving aperture axis generally parallel to the first rod-receiving axis. The second bracket mounts to a second rib and includes a second rib-receiving aperture, a second rod-receiving aperture, and a second support member-receiving aperture. The second rib-receiving aperture includes a second rib-receiving axis. The second rod-receiving aperture includes a second rod-receiving axis generally perpendicular to the second rib-receiving axis. The second support member-receiving aperture includes a second support member-receiving aperture axis generally parallel to the second rod-receiving axis. The plate includes first and second channels and is operable to clamp the first rib in the first channel and in the first rib-receiving aperture, and clamp the second rib in the second channel and in the second rib-receiving aperture. The sternal implant is mounted to a sternum and includes a third rod-receiving aperture having a third rod-receiving axis.

In yet another configuration, the present disclosure provides an apparatus for the correction of chest deformities. The apparatus includes a rib implant for mounting to a rib, a sternal implant for mounting to a sternum, and a rod member. The rib implant includes a rib-receiving aperture having a rib-receiving axis, a first rod-receiving aperture having a first rod-receiving axis, and a support member-receiving aperture having a support member-receiving axis extending in a direction substantially perpendicular to the rib-receiving axis and the first rod-receiving axis. The sternal implant includes a second rod-receiving aperture having a second rod-receiving axis extending in a direction substantially parallel to the rib-receiving axis and the first rod-receiving axis. The rod member includes a first end adjustably disposed in the first rod-receiving aperture and a second end adjustably disposed in the second rod receiving aperture.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 1:
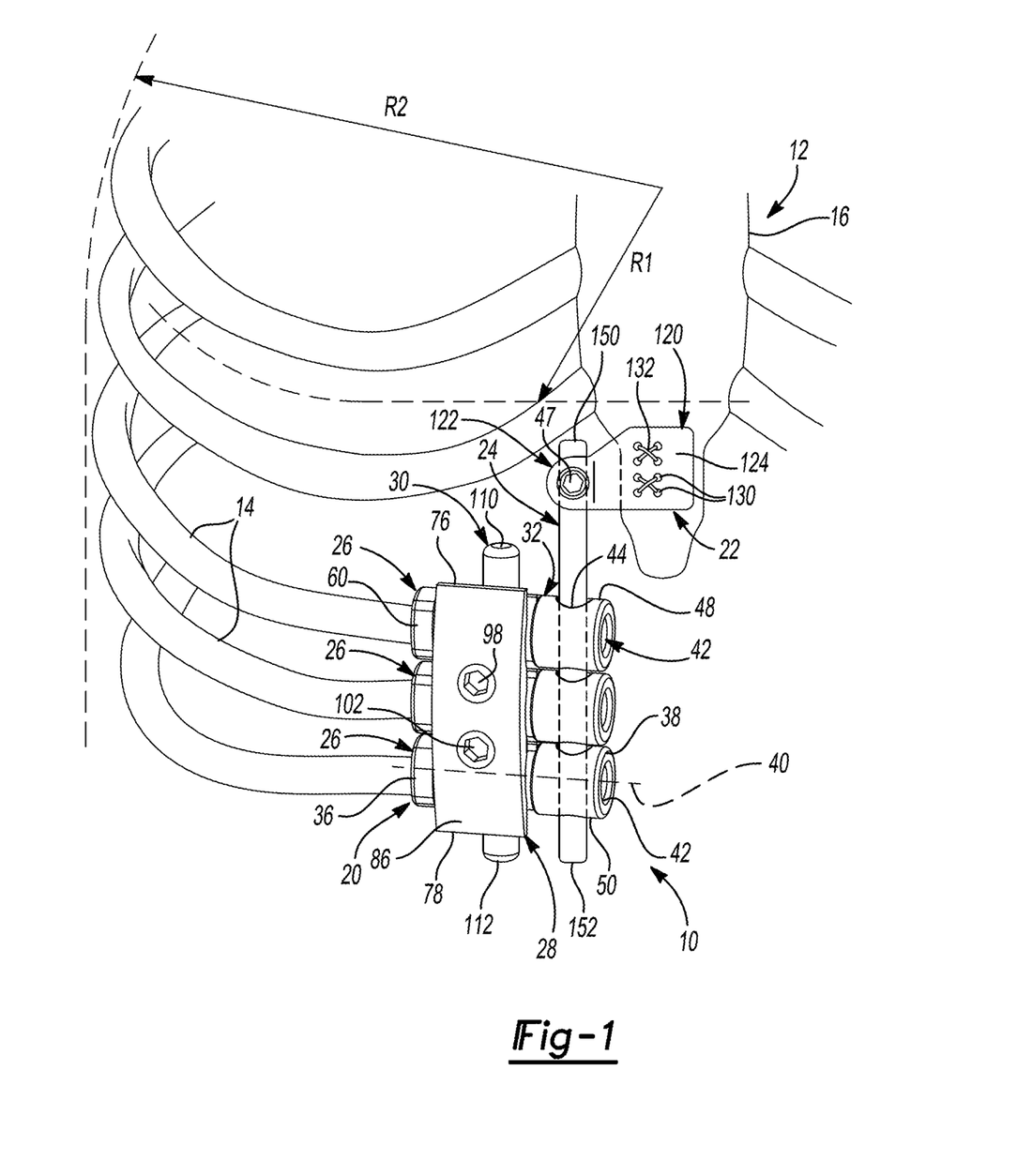
FIG. 1 is a perspective view of a rib reconstruction assembly in accordance with the principles of the present disclosure.
Figure 2:
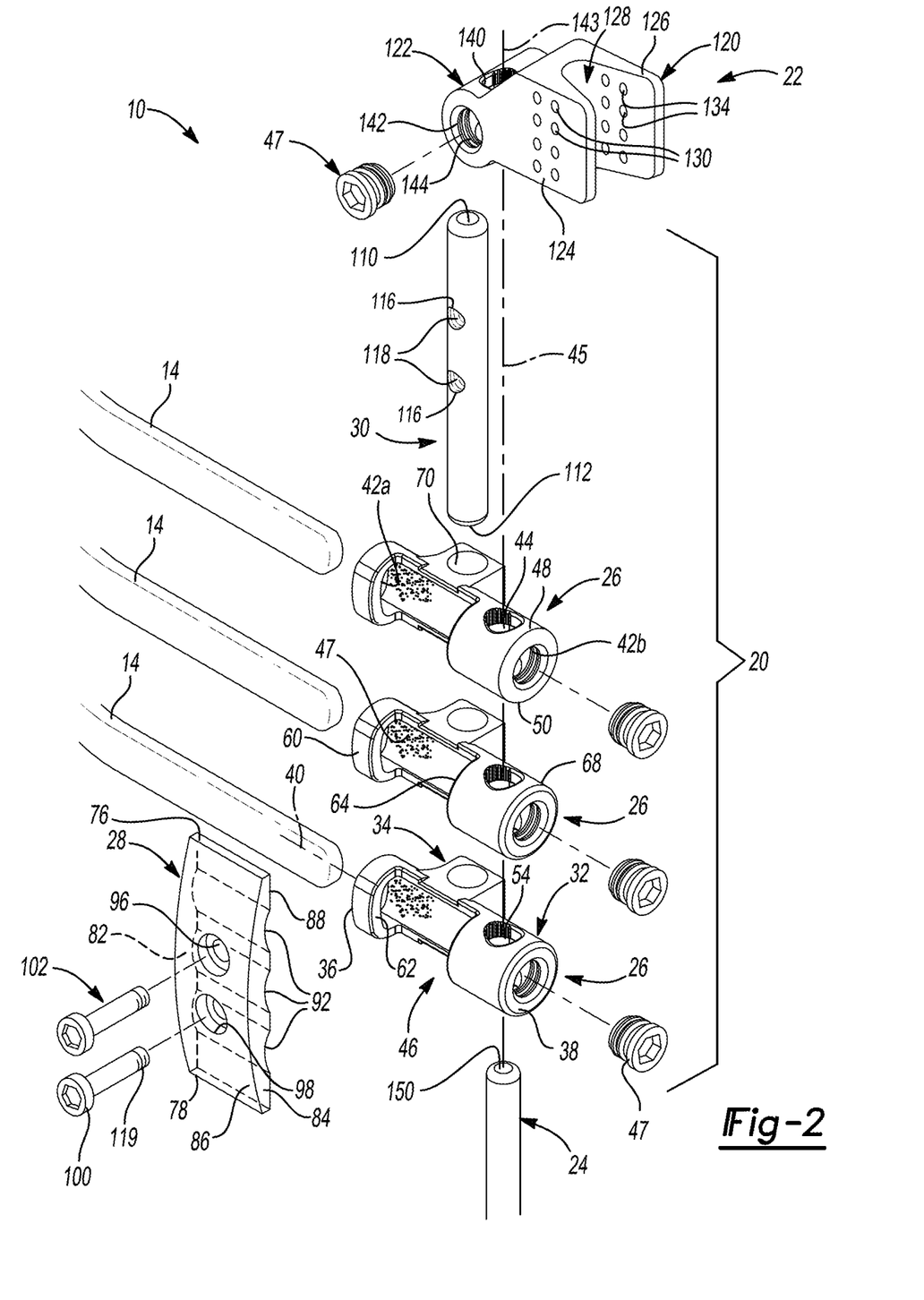
FIG. 2 is an exploded view of the rib reconstruction assembly of FIG. 1.

With reference to FIGS. 1 and 2, a rib reconstruction assembly 10 is provided in accordance with the principles of the present disclosure. The rib reconstruction assembly 10 is shown operatively associated with a thoracic cavity 12, including a plurality of ribs 14, and a sternum 16. The thoracic cavity 12 may include a first radius of curvature R1 extending along, and at least partially defined by, one of the ribs 14, and a second radius of curvature R2 extending from and between at least two of the ribs 14. As will be explained in more detail below, the rib reconstruction assembly 10 may be used to treat and repair defects and abnormalities in the thoracic cavity 12, including abnormalities in the first and second radii of curvature R1, R2. By way of example only, the rib reconstruction assembly 10 may be used to treat such conditions as pectus excavatum, fractured or fused ribs, Poland syndrome, and oncological cases.

The rib reconstruction assembly 10 may include a plate subassembly 20, a sternal implant 22, and an elongate member or rod 24. The plate subassembly 20 may include a first rib implant or bracket 26, a second rib implant or plate 28, and a support member 30. As will be explained in more detail below, in an assembled configuration, the plate subassembly 20 may be coupled to the sternal implant 22 and to at least one of the ribs 14, while the sternal implant 22 may be coupled to the sternum 16.

The bracket 26 may include a body portion 32 and a flange portion 34. The body portion 32 may extend from a proximal or lateral end 36 to a distal or medial end 38 along a first axis 40. As illustrated, in some configurations, the body portion 32 may include a generally cylindrical construct. It will be appreciated, however, that the body portion 32 may include other shapes and configurations within the scope of the present disclosure. With reference to FIG. 2, the body portion 32 may further include a first aperture 42, a second aperture 44, and a slot or window 46. The first aperture 42 may be formed in the lateral end 36 and may extend along the first axis 40 within the body portion 32. As illustrated, in some configurations, the first aperture 42 may be a through-hole extending from and between the lateral and medial ends 36, 38 of the body portion 32. In other configurations, the first aperture 42 may include a rib-receiving portion 42a extending along the first axis 40 from the lateral end 36, and a fastener-receiving portion 42b extending along the first axis 40 from the medial end 38. In this regard, the rib-receiving portion 42a and the fastener-receiving portion 42b may each extend partially through the body portion 32. As will be explained in more detail below, the rib-receiving portion 42a of the first aperture 42 may be sized and shaped to receive one of the ribs 14. The fastener-receiving portion 42b may be sized and shaped to receive a set screw 47 or other suitable fastener for securing the rod 24 within the second aperture 44. In this regard, the fastener-receiving portion 42b may be internally threaded.

The body portion 32 may further include a porous plasma layer or coating 49 formed within the rib-receiving aperture 42. The porous plasma coating 49 can help to promote bone ingrowth between the bracket 26 and the rib 14, and thus help to secure the bracket 26 to the rib 14.

The second aperture 44 may be formed near the medial end 38 of the body portion 32 and extend along a second axis 45. The second aperture 44 may be sized and shaped to receive the rod 24. Accordingly, references herein to the rod-receiving aperture 44 will be understood to mean the second aperture 44. The second aperture 44 may be formed between the medial end 38 and the window 46, and may extend from an upper side 48 (relative to the view in FIG. 1) of the body portion 32 to a lower side 50 of the body portion 32. As illustrated, the second aperture 44 may be a through-hole, such that the second aperture 44 may intersect, or otherwise be in communication with, the first aperture 42. In this regard, in some configurations the second axis 45 may extend in a direction substantially perpendicular to the first axis 40. As illustrated in FIG. 2, the second aperture 44 may include a serrated portion 54 for gripping or otherwise helping to secure the rod 24 within the second aperture 44.

The window 46 may be formed in the body portion 32 between the lateral end 36 and the second aperture 44. In this regard, the window 46 may be formed in a front or anterior side 60 (relative to the view in FIG. 1) of the body portion 32, and may be at least partially defined by a first sidewall 62 and a second sidewall 64 opposing the first sidewall 62. The first and second sidewalls 62, 64 may be substantially planar and spaced such that the plate 28 can be disposed within the window 46, as will be explained in more detail below. The window 46 may open into, or otherwise be in communication with, the first aperture 42.

As illustrated in FIG. 2, the flange portion 34 of the bracket 26 may be coupled to the body portion 32. In some configurations, the flange portion 34 may be integrally and monolithically formed with the body portion 32. In this regard, the flange portion 34 may be coupled to, and/or extend from, a rear or posterior side 68 (relative to the view in FIG. 1) of the body portion 32, in a direction substantially perpendicular to the first axis 40. The flange portion 34 may include a third aperture 70. The third aperture 70 may be a through-hole extending in a direction substantially perpendicular to the first aperture 42 and substantially parallel to the second aperture 44. The third aperture 70 may be sized and shaped to receive the support member 30. Accordingly, references herein to the support member-receiving aperture 70 will be understood to mean the third aperture 70.

The plate 28 may extend from a proximal end 76 to a distal end 78, and may include a first lateral side 82, a second lateral side 84, an anterior side 86, and a posterior side 88. The second lateral side 84 may oppose the first lateral side 82, such that a distance between the first and second lateral sides 82, 84 is substantially equal to, or slightly less than, a distance between the first and second sidewalls 62, 64 of the window 46. In this regard, in the assembled configuration, the plate 28 may be disposed within the window 46, as illustrated in FIG. 1.

The anterior side 86 of the plate 28 may include a convex curvature extending from the proximal end 76 to the distal end 78, such that in the assembled configuration the anterior side extends at least partially about the first axis 40. In this regard, it will be appreciated that the anterior side 86 may define a radius of curvature R3. The radius of curvature R3 may be substantially equal to the second radius of curvature R2 of the thoracic cavity 12.

The posterior side 88 of the plate 28 may include at least one groove or channel 92 formed therein. As illustrated in FIG. 2, in some configurations the posterior side 88 may include three channels 92. It will be appreciated, however, that the posterior side 88 may include more or fewer than three channels 92 within the scope of the present disclosure. The channel 92 may extend from and between the first and second lateral sides 82, 84, and may be sized and shaped to receive one of the ribs 14.

The plate 28 may further include at least one through-hole or aperture 96 extending from and between the anterior and posterior sides 86, 88. As illustrated, the aperture 96 may extend between adjacent channels 92, such that the aperture 96 does not intersect the channel 92. In some configurations, the aperture 96 may include a counterbore portion 98 to receive a head portion 100 of a fastener 102 (e.g., screw or bolt).

Figure 3:
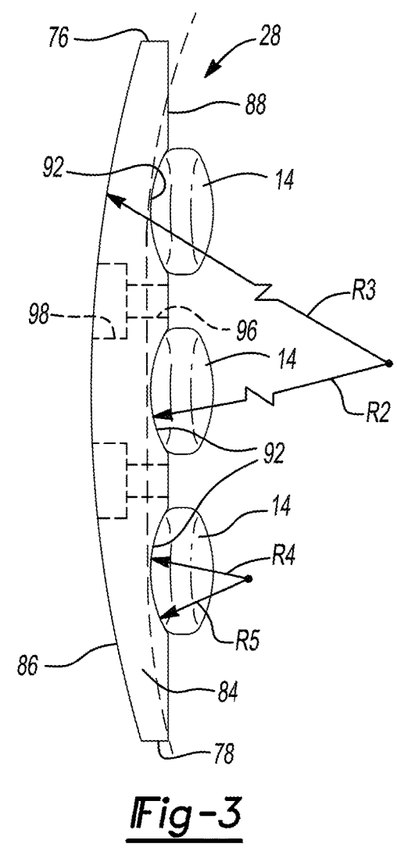
FIG. 3 is an end view of a plate of the rib reconstruction assembly of FIG. 1.

The bracket 26 and/or the plate 28 may be manufactured using an additive manufacturing process, such as three-dimensional printing. In this regard, the bracket 26 and/or the plate 28 may be constructed from a suitable biocompatible material, such as a biocompatible polymer. A method of manufacturing the bracket 26 and/or the plate 28 may include obtaining an image of a patient's thoracic cavity 12, including the sternum 16 and the ribs 14. The image may be produced from an X-ray, an MRI, an ultrasound, or other suitable image capturing technique. The image may include data representing certain characteristics of the thoracic cavity 12 (e.g., radius R1, radius R2, etc.) and/or data representing certain characteristics of the ribs 14 (e.g., shapes, sizes, location, etc.). In some configurations, the data may include a fourth radius of curvature of one or more of the ribs 14. The image, and/or the data representing the image, may be communicated to an additive manufacturing machine (e.g., a three-dimensional printer). The additive manufacturing machine may manipulate or otherwise use the data in order to produce a bracket 26 and/or a plate 28 having characteristics (e.g., shape, size, etc.) that match, or are otherwise compatible with, the certain characteristics of the thoracic cavity 12 and/or the ribs 14 of the patient. In this way, the bracket 26 and/or the plate 28 can be manufactured or otherwise customized for a specific patient, such that the rib-receiving portion 42a of the bracket 26 and/or the channels 92 of the plate 28 match, or are otherwise compatible with, the characteristics of the patient's ribs 14. For example, as illustrated in FIG. 3, a fourth radius of curvature R4 of at least one of the channels 92 may be substantially equal to a fifth radius of curvature R5 of a least one of the ribs 14. While the manufacturing process is described herein as being an additive manufacturing process, it will also be appreciated that the bracket 26 and/or the plate 28 may be manufactured, or otherwise customized, using other suitable manufacturing processes, such as injection molding, machining, and casting.

The support member 30 may extend from a proximal end 110 to a distal end 112. While the support member 30 is illustrated as having a generally cylindrical construct, it will be appreciated that the support member 30 may include other shapes within the scope of the present disclosure. In this regard, the support member 30 may be sized and shaped such that the support member 30 can be received by and through the third aperture 70 of the bracket 26. In this regard, in the assembled configuration, the support member 30 may be disposed within the third aperture 70 such that the support member 30 extends substantially perpendicular to the first axis 40. The support member 30 may further include at least one through hole or aperture 116. The number of apertures 116 may equal the number of apertures 96 formed in the plate 28, such that the fasteners 102 extend through the apertures 96 and through the apertures 116 to secure the plate 28 to the support member 30. In this regard, the aperture 116 may include a threaded portion 118 to threadingly engage a threaded portion 119 of the fastener 102.

The sternal implant 22 may include a sternum-receiving portion 120 and a rod-receiving portion 122. The sternum-receiving portion 120 may include a first or anterior arm 124 and a second or posterior arm 126. The first and second arms 124, 126 may define a channel or cavity 128 therebetween. As illustrated, the cavity 128 may define a U-, C- or J-shaped cross section. In this regard, the cavity 128 may be sized and shaped to receive the sternum 16 between the first and second arms 124, 126. In the assembled configuration, the first arm 124 may be disposed on an anterior side of the sternum 16, and the second arm 126 may be disposed on the posterior side of the sternum 16.

The first arm 124 may include at least one through-hole or aperture 130. As illustrated, in some configurations, the first arm 124 may include eight apertures 130. It will be appreciated, however, that the first arm 124 may include more or fewer than eight apertures 130 within the scope of the present disclosure. In this regard, the apertures 130 may be arranged in a series of rows and/or columns. The apertures 130 may be sized and shaped to receive a suture 132 or other suitable fastener (e.g., screw or bolt) for securing the sternal implant 22 to the sternum 16.

The second arm 126 may include at least one through-hole or aperture 134. As illustrated, in some configurations, the second arm 126 may include eight apertures 134. It will be appreciated, however, that the second arm 126 may include more or fewer than eight apertures 134 within the scope of the present disclosure. In this regard, the apertures 134 may be arranged in a series of rows and/or columns. The apertures 134 may be sized and shaped to receive the suture 132 or other suitable fastener (e.g., screw or bolt) for securing the sternal implant 22 to the sternum 16. As will be explained more detail, below, the suture 132 may extend from the apertures 130 of the first arm 124 to the apertures 134 of the second arm 126 to secure the sternal implant to the sternum 16.

The rod receiving portion 122 may be integrally formed with the sternum receiving portion 120. In this regard, the rod receiving portion 122 and the sternum receiving portion 120 may define a monolithic construct. The rod receiving portion 122 may include first through-hole or aperture 140 and a second through-hole or aperture 142. The first aperture 140 may extend along a third axis 143. As will be explained in more detail, below, the first aperture 140 may be sized and shaped to receive the rod 24. Accordingly, references herein to the rod-receiving aperture 140 will be understood to mean the first aperture 140. In this regard, in some configurations, the first aperture 140 may include a substantially cylindrical construct. The second aperture 142 may extend in a direction substantially perpendicular to the third axis 143, and may intersect or otherwise communicate with the first aperture 142. The second aperture 142 may include a threaded portion 144 for threadingly receiving the set screw 47 to help secure the rod 24 within the first aperture 140.

The sternal implant 22 may be manufactured using an additive manufacturing process, such as three-dimensional printing. In this regard, the sternal implant 22 may be constructed from a suitable biocompatible material, such as a biocompatible polymer. A method of manufacturing the sternal implant 22 may include obtaining an image of a patient's thoracic cavity 12, including the sternum 16. The image may be produced from an X-ray, an MRI, an ultrasound, or other suitable image capturing technique. The image may include data representing certain characteristics of the thoracic cavity 12 (e.g., radius R1, radius R2, etc.) and/or data representing certain characteristics of the sternum 16 (e.g., shape, size, location, etc.). The image, and/or data representing the image, may be communicated to an additive manufacturing machine (e.g., a three-dimensional printer). The additive manufacturing machine may manipulate or otherwise use the data in order to produce or construct a sternal implant 22 having characteristics (e.g., shape, size, etc.) that match, or are otherwise compatible with, the certain characteristics of the thoracic cavity 12 and/or the sternum 16. In this way, the sternal implant 22 can be manufactured or otherwise customized for a specific patient. For example, the characteristics of the first arm 124 and/or the second arm 126 can be customized such that the cavity 128 of the sternal implant 22 matches, or is otherwise compatible with, the characteristics of the patient's sternum 16. While the manufacturing process is described herein as being an additive manufacturing process, it will also be appreciated that the sternal implant 22 may be manufactured, or otherwise customized, using other suitable manufacturing processes, such as injection molding, machining, and casting.

The rod 24 may be an elongate, flexible member having a lateral or proximal end 150 and a medial or distal end 152. In this regard, the rod 24 may define a length L between the proximal and distal ends 150, 152. The rod 24 may be formed from a flexible metallic material, such as steel, for example. It will also be appreciated that the rod 24 may be formed from other flexible materials within the scope of the present disclosure. In some configurations, the rod 24 may be the "connecting rod 18" disclosed in commonly owned U.S. patent application Ser. No. 14/253,917, the disclosure of which is incorporated herein by reference in its entirety. As will be explained in more detail below, in the assembled configuration, the rod 24 may be disposed and secured to the plate subassembly 20 and the sternal implant 22.

As illustrated in FIG. 1, in the assembled configuration, the plate subassembly 20 may be secured to the rib 14, and the sternal implant 22 may be secured to the sternum 16. The rod 24 may be secured to the plate subassembly 20 and to the sternal implant 22 in the manner described above. Specifically, the rib 14 may be disposed within the rib-receiving aperture 42 of the bracket 26. The plate 28 may be disposed within the window 46, such that the rib 14 is secured between the plate 28 and the bracket 26. In this regard, the fastener 102 may be placed within the aperture 96 of the plate 28 and within the aperture 116 of the support member 30 to secure the plate 28 to the support member 30, and to clamp the rib 14 between the plate 28 and the bracket 26. The sternum 16 may be disposed and secured within the cavity 128 of the sternal implant 22. The suture 132 may be disposed within the apertures 130 of the first arm 124 and the apertures 134 of the second arm 126, and wrapped around the sternum 16, to secure the sternal implant 22 to the sternum 16.

The rod 24 may be bent or otherwise configured to have a pre-determined or desired shape. In this regard, the rod 24 may be bent to have a radius of curvature substantially equal to the desired radii of curvature R1 and/or R2 of the thoracic cavity 12. Thereafter, the proximal end 150 of the rod 24 may be placed within the first aperture 140 of the sternal implant 22, and the distal end 152 of the rod 24 may be placed within the second aperture 44 of the bracket 26. The set screws 47 may be assembled within the second aperture 142 and the second portion 42b of the first aperture 42 to secure the rod 24 to the sternal implant 22 and the bracket 26, respectively. In the assembled configuration, the second axis 45 may be substantially aligned with, or otherwise parallel to, the third axis 143.

It will be appreciated that a distance between the bracket 26 and the sternal implant 22, as measured along the second axis 45, can be adjusted by changing the location of the sternal implant 22 relative to the sternum 16 and/or by changing the location of the bracket 26 relative to the ribs 14. As the distance between the bracket 26 and the sternal implant 22 is adjusted along the second axis 45, the length L of the rod 24 can be adjusted such that the distal end 152 of the rod 24 may be secured within the second aperture 44 of the bracket 26, and the proximal end 150 of the rod 24 may be secured within the first aperture 140 of the sternal implant 22. In some configurations, the rod 24 can be trimmed or otherwise cut, such that the distal end 152 of the rod 24 can be secured within the second aperture 44, and the proximal end 150 of the rod 24 may be secured within the first aperture 140. In this regard, it will also be appreciated that the rod 24 can translate, or otherwise be adjusted, within the second aperture 44 in a direction substantially parallel to the second axis 45, and/or translated, or otherwise be adjusted, within the first aperture 140 in a direction substantially parallel to the third axis 143, such that the distal end 152 of the rod 24 can be secured within the second aperture 44, and the proximal end 150 of the rod 24 may be secured within the first aperture 140. In this way, the rib reconstruction assembly 10, including the flexible or bendable rod 24, can allow a surgeon to effectively treat and repair variously-sized defects and abnormalities in the thoracic cavity 12, including defects in the radius of curvatures R1, R2. (i.e., horizontally extending defects and vertically extending defects).

Figure 4:
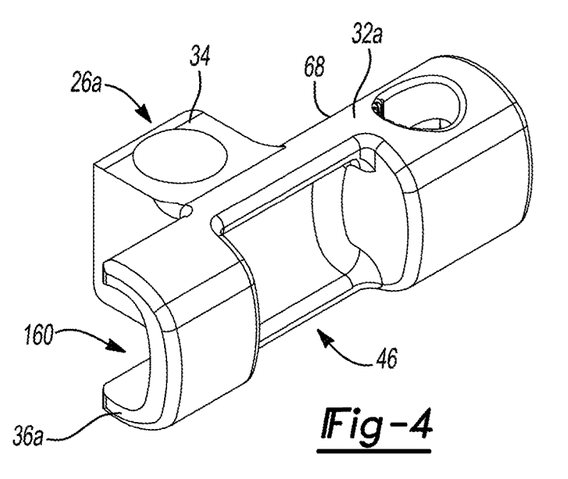
FIG. 4 is perspective view of a rib coupler or bracket for use with the rib reconstruction assembly of FIG. 1.

With reference to FIG. 4, another bracket 26a is provided that may be used with the rib reconstruction assembly 10. In this regard, one or more brackets 26a may be used in place of, or in combination with, one or more brackets 26. The structure and function of the bracket 26a may be similar or identical to the structure and function of the bracket 26 described above, apart from any exceptions described below and/or shown in the figures. Accordingly, similar features will not be described again in detail. Like reference numerals are used hereinafter and in the drawings to identify like components, while like reference numerals containing letter extensions are used to identify those components that have been modified.

The bracket 26a may include a second window 160 formed in the posterior side 68a of the body portion 32a. The window 160 may extend from the lateral end 36a to the flange portion 34, such that the body portion 32a defines a U-shaped cross section extending from the lateral end 36a to the flange portion 34.

Figure 5:
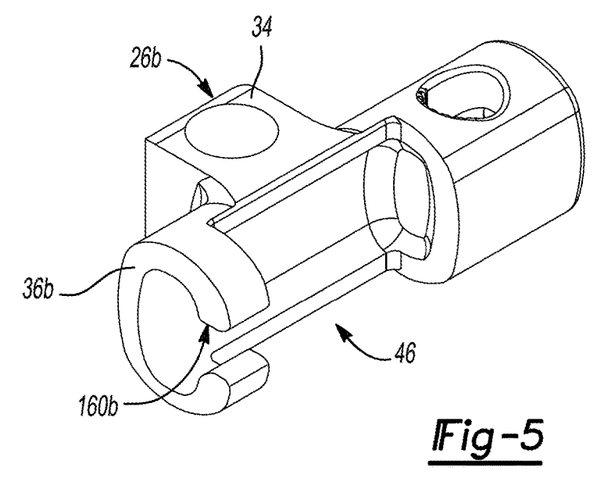
FIG. 5 is perspective view of another rib coupler or bracket for use with the rib reconstruction assembly of FIG. 1.

With reference to FIG. 5, another bracket 26b is provided that may be used with the rib reconstruction assembly 10. In this regard, one or more brackets 26b may be used in place of, or in combination with, one or more brackets 26 or 26a. The structure and function of the bracket 26b may be similar or identical to the structure and function of the bracket 26 described above, apart from any exceptions described below and/or shown in the figures. Accordingly, similar features will not be described again in detail. Like reference numerals are used hereinafter and in the drawings to identify like components, while like reference numerals containing letter extensions are used to identify those components that have been modified.

The bracket 26b may include a second window 160b formed in the anterior side 68b of the body portion 32b. The window 160b may extend from the lateral end 36b to the window 46, such that the body portion 32b defines a C-shaped cross section extending from the lateral end 36b to the window 46.

Figure 6:
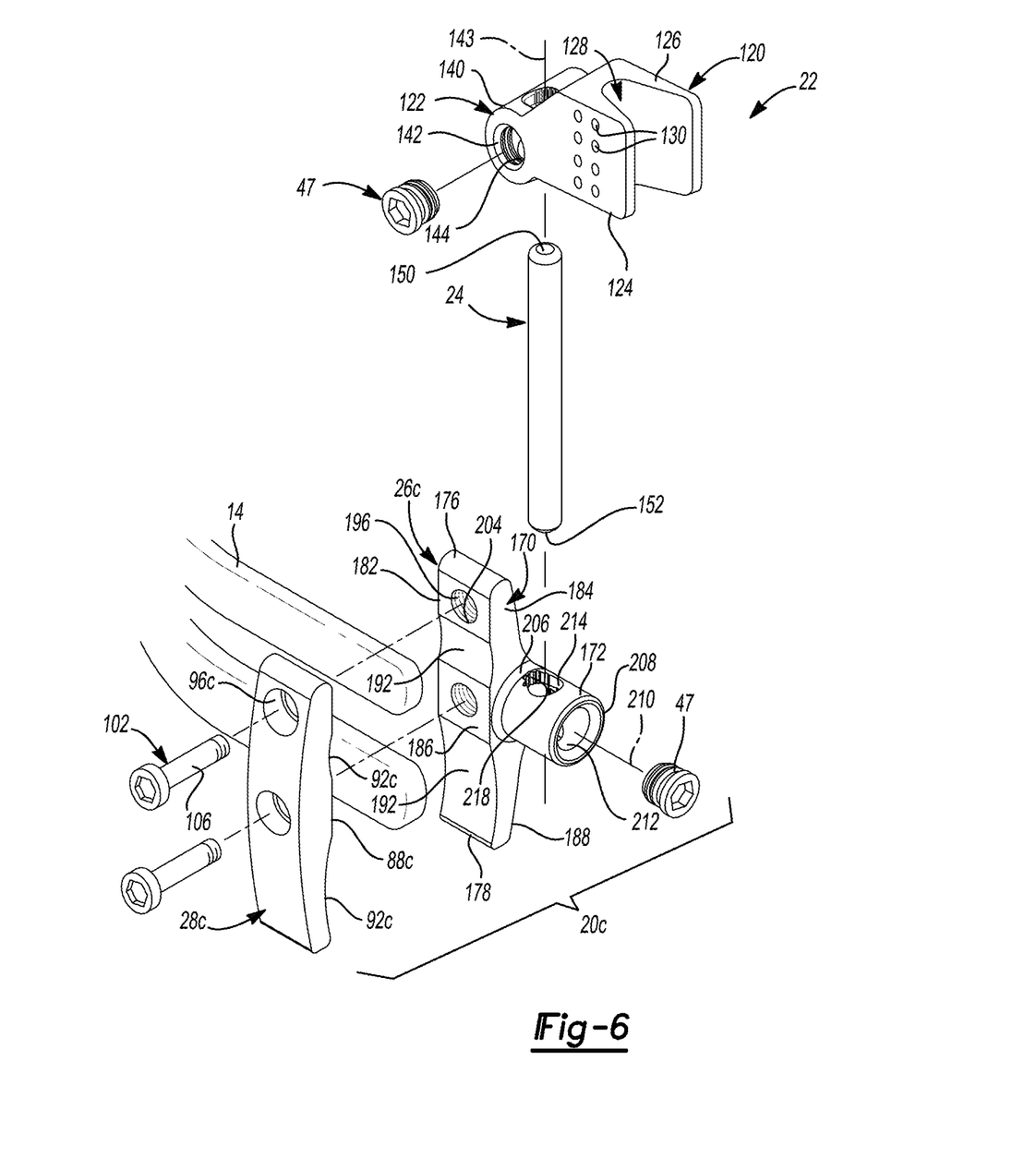
FIG. 6 is an exploded view of a plate subassembly for use with the rib reconstruction assembly of FIG. 1.

With reference to FIG. 6, another plate subassembly 20c is provided. As will be explained in more detail below, the plate subassembly 20c may be used with the sternal implant 22 and the rod 24. The structure and function of the plate subassembly 20c may be similar or identical to the structure and function of the plate subassembly 20 described above, apart from any exceptions described below and/or shown in the figures. Accordingly, similar features will not be described again in detail. Like reference numerals are used hereinafter and in the drawings to identify like components, while like reference numerals containing letter extensions are used to identify those components that have been modified.

The plate subassembly 20c may include a first rib implant or bracket 26c and a second rib implant or plate 28c. The bracket 26c may include a plate portion 170 and a flange portion 172. The plate portion 170 may extend from a proximal end 176 to a distal end 178, and may include a first lateral side 182, a second lateral side 184, an anterior side 186, and a posterior side 188. The second lateral side 184 may oppose the first lateral side 182. The anterior side 186 of the plate portion 170 may include at least one groove or channel 192 formed therein. As illustrated in FIG. 5, in some configurations the anterior side 186 may include two channels 192. It will be appreciated, however, that the anterior side 186 may include more or fewer than two channels 192 within the scope of the present disclosure. The channel 192 may extend from and between the first and second lateral sides 182, 184, and may be sized and shaped to receive one of the ribs 14.

The plate portion 170 may further include at least one through-hole or aperture 196 extending from and between the anterior and posterior sides 186, 188. As illustrated, the aperture 196 may extend between adjacent channels 192, such that the aperture 196 does not intersect the channel 192. The aperture 196 may include a threaded portion 204 to receive the stem portion 106 of the fastener 102.

The flange portion 172 may extend from a lateral end 206 to a medial end 208 along a first axis 210. The lateral end 206 may be adjacent and/or integrally formed with, the second lateral side 184 of the plate portion 170. As illustrated, in some configurations, the flange portion 172 may include a generally cylindrical construct. It will be appreciated, however, that the flange portion 172 may include other shapes and configurations within the scope of the present disclosure. The flange portion 172 may further include a first aperture 212 and a second aperture 214. The first aperture 212 may be formed in the medial end 208 and may extend substantially parallel to the first axis 210 within the flange portion 172. The first aperture 212 may be sized and shaped to receive the set screw 47. Accordingly, in an assembled configuration, the set screw 47 can directly engage the distal end 152 of the rod 24, to secure the rod 24 within the aperture 214.

The second aperture 214 may extend in a direction substantially perpendicular to the first axis 210. In this regard, the second aperture 214 may be formed between the lateral and medial ends 206, 208 of the flange portion 172. In this regard, the second aperture 214 may be a through-hole, such that the second aperture 214 may be in communication with the first aperture 212. The second aperture 214 may include a serrated portion 218.

The plate 28c or the plate 28 may be used with the bracket 26c. In this regard, the structure and function of the plate 28c may be similar or identical to the structure and function of the plate 28 described above, apart from any exceptions described below and/or shown in the figures. Accordingly, similar features will not be described again in detail. Like reference numerals are used hereinafter and in the drawings to identify like components, while like reference numerals containing letter extensions are used to identify those components that have been modified.

The posterior side 88c of the plate 28c may include at least one groove or channel 92c formed therein. As illustrated, in some configurations the posterior side 88c may include two channels 92c. It will be appreciated, however, that the posterior side 88 may include more or fewer than three channels 92c within the scope of the present disclosure. In this regard, it will be appreciated that the number of channels 92c may correspond to the number of channels 192 in the plate portion 170 of the bracket 26c, such that a rib 14 can be clamped within and between the channels 92c, 192.

The plate 28c may further include at least one through-hole or aperture 96c extending from and between the anterior and posterior sides 86c, 88c. As illustrated, the aperture 96c may extend between adjacent channels 92c, such that the aperture 96c does not intersect the channel 92c. In an assembled configuration, the apertures 96c may be aligned with the apertures 196 in the plate portion 170.

Figure 7:
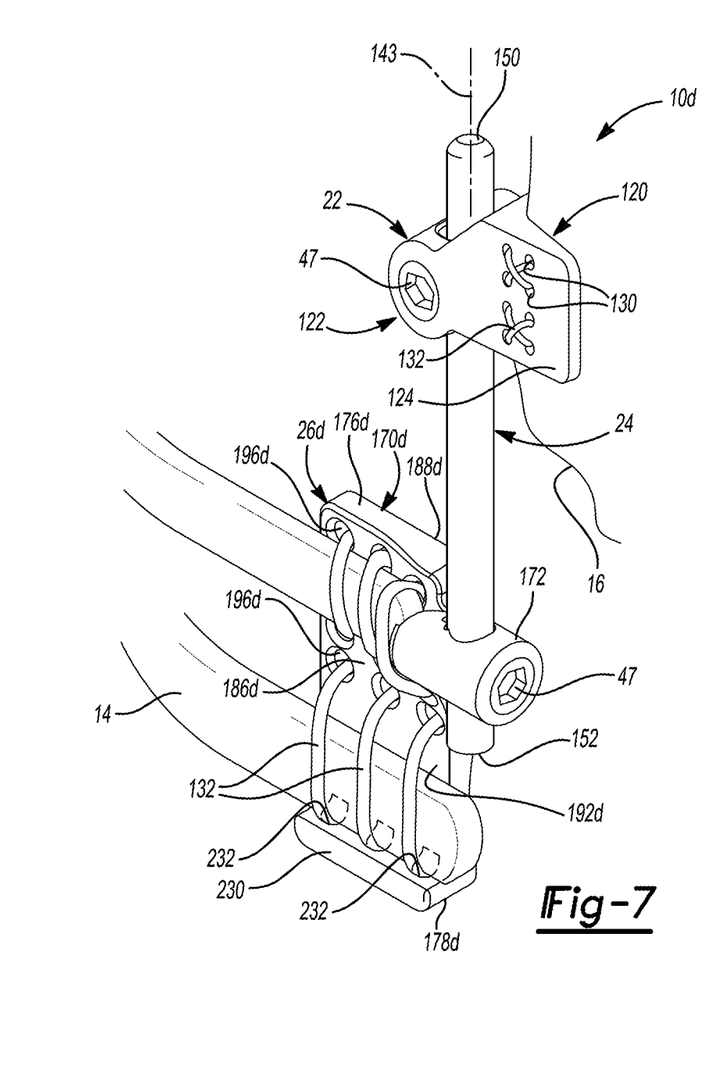
FIG. 7 is a perspective view of another plate subassembly for use with the rib reconstruction assembly of FIG. 1.
Figure 8:
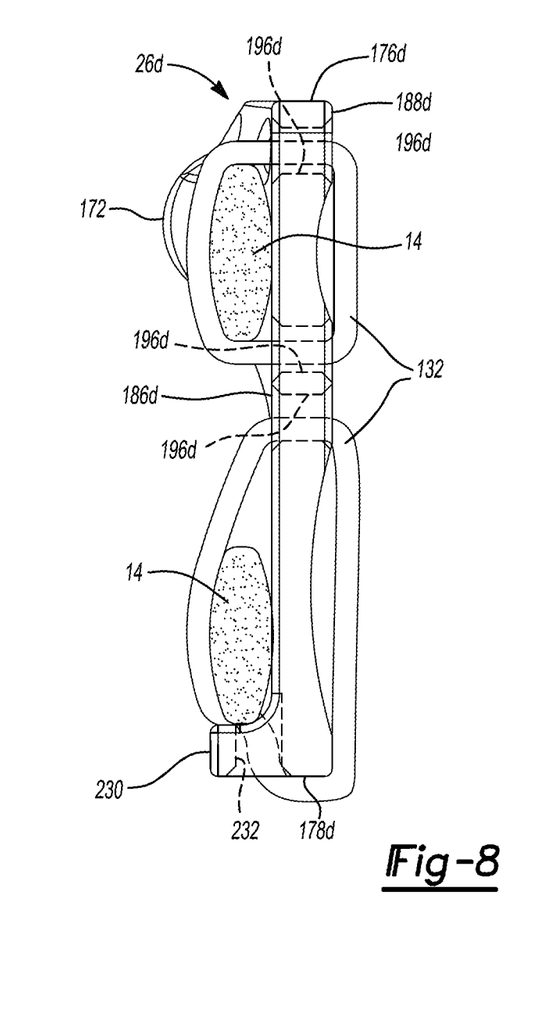
FIG. 8 is an end view of the plate subassembly of FIG. 7.

With reference to FIGS. 7 and 8, another rib reconstruction assembly 10d, including a first rib implant or bracket 26d is provided. As will be explained in more detail below, the bracket 26d may be used with the sternal implant 22 and the rod 24. The structure and function of the bracket 26d may be similar or identical to the structure and function of the bracket 26c described above, apart from any exceptions described below and/or shown in the figures. Accordingly, similar features will not be described again in detail. Like reference numerals are used hereinafter and in the drawings to identify like components, while like reference numerals containing letter extensions are used to identify those components that have been modified.

The bracket 26d may include a plate portion 170d and the flange portion 172. The plate portion 170d may extend from a proximal end 176d to a distal end 178d, and may include an anterior side 186d and a posterior side 188d. The anterior side 186d may include at least one groove or channel 192d formed therein. The distal end 178d may include a flange 230 extending from the anterior side 186d of the plate portion 170d. The flange 230 may include at least one aperture 232 extending therethrough. As illustrated, in some configurations the flange 230 may include three apertures. It will be appreciated, however, that the flange portion may include more or fewer than three apertures within the scope of the present disclosure.

The plate portion 170d may further include at least one through-hole or aperture 196d extending from and between the anterior and posterior sides 186d, 188d. As illustrated, the aperture 196d may extend between adjacent channels 192d, such that the aperture 196 does not intersect the channel 192d. In this regard, the plate portion 170d may include three apertures 196 disposed between the proximal end 176d and a first channel 192d, and six apertures 196 disposed between the first channel 192d and a second channel 192d. It will be appreciated, however, that the plate portion 170d may include more or fewer than the aforementioned number of apertures disposed between the proximal end 176d and the first channel 192d, and between the first channel 192d and the second channel 192d. In an assembled configuration, the ribs 14 may be disposed within the channels 192d. The sutures 132 may extend through the apertures 196, and around the ribs 14, to secure the ribs 14 to the bracket 26d.

The bracket 26d may be manufactured using an additive manufacturing process, such as three-dimensional printing. In this regard, the bracket 26d may be constructed from a suitable biocompatible material, such as a biocompatible polymer. A method of manufacturing the bracket 26d may include obtaining an image of a patient's thoracic cavity 12 in the manner described above. The image may include data representing certain characteristics of the ribs 14, such as a radius of curvature. The image, and/or data representing the image, may be communicated to an additive manufacturing machine (e.g., a three-dimensional printer). The additive manufacturing machine may manipulate or otherwise use the data in order to produce a bracket 26d having characteristics (e.g., shape, size, etc.) that match, or are otherwise compatible with, the certain characteristics of the patient's thoracic cavity 12 and/or ribs 14. In this way, the bracket 26d can be manufactured or otherwise customized for a specific patient.

Figure 9:
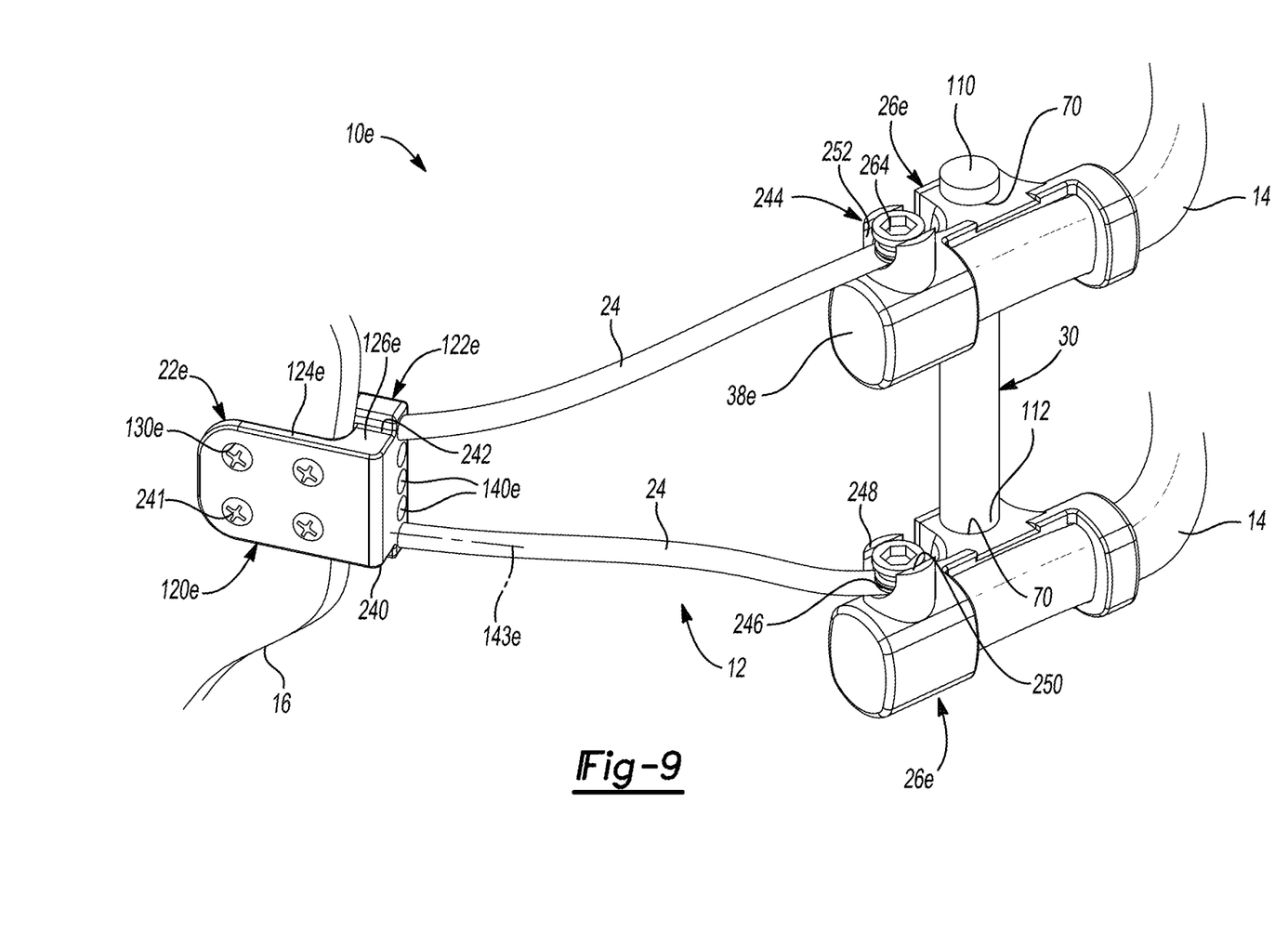
FIG. 9 is a perspective view of another rib reconstruction assembly in accordance with the principles of the present disclosure.
Figure 10:
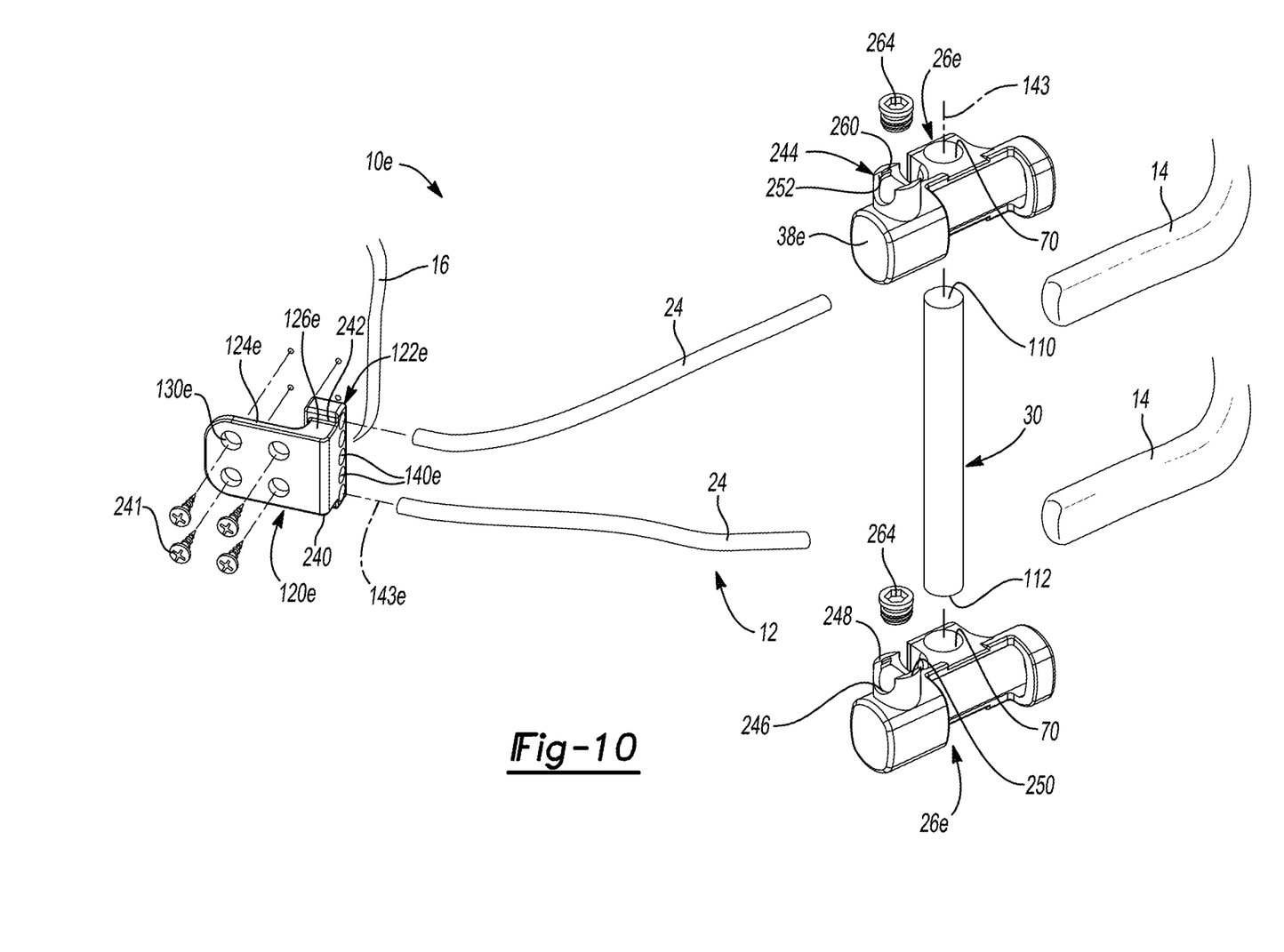
FIG. 10 is an exploded view of the rib reconstruction assembly of FIG. 9.

With reference to FIGS. 9 and 10, another rib reconstruction assembly 10e is provided. The rib reconstruction assembly 10e is shown operatively associated with the thoracic cavity 12, including the plurality of ribs 14, and the sternum 16. As will be explained in more detail below, the rib reconstruction assembly 10e may be used to treat large defects in the thoracic cavity 12.

The rib reconstruction assembly 10e may include a sternal implant 22e, the rod 24, a bracket 26e, and the support member 30. The structure and function of the sternal implant 22e may be similar or identical to the structure and function of the sternal implant 22 described above, apart from any exceptions described below and/or shown in the figures. Accordingly, similar features will not be described again in detail. Like reference numerals are used hereinafter and in the drawings to identify like components, while like reference numerals containing letter extensions are used to identify those components that have been modified.

The sternal implant 22e may include a sternum receiving portion 120e and a rod receiving portion 122e. The sternum receiving portion 120e may include a first arm 124e and a second arm 126e. The first and second arms 124e, 126e may define an L-shaped cross section, shaped to receive the sternum 16 between the first and second arms 124e, 126e. In this regard, the second arm 126e may extend from a distal end 240 to a proximal end 242 in a first direction. The proximal end 242 may be adjacent to, and integrally formed with, the first arm 124e. In the assembled configuration, the first arm 124e may be disposed on an anterior side of the sternum 16, and the second arm 126e may be disposed on a lateral side of the sternum 16.

The first arm 124e may include at least one through-hole or aperture 130e. As illustrated, in some configurations, the first arm 124e may include four apertures 130e. It will be appreciated, however, that the first arm 124e may include more or fewer than four apertures 130e within the scope of the present disclosure. In this regard, the apertures 130e may be arranged in a series of rows and/or columns. The apertures 130e may be sized and shaped to receive the suture 132 or a suitable mechanical fastener 241 (e.g., screw or bolt) for securing the sternal implant 22e to the sternum 16.

The rod-receiving portion 122e may extend from, and be integrally formed with, the second arm 126e. In this regard, the rod-receiving portion 122e may include a flanged portion of the sternal implant 22e. The rod-receiving portion 122e and the sternum receiving portion 120e may define a monolithic construct. The rod-receiving portion 122e may include at least one first through-hole or aperture 140e extending along a third axis 143e. As will be explained in more detail, below, the first aperture 140e may be sized and shaped to receive the rod 24. In the assembled configuration, the first aperture 140e may extend in a substantially horizontal direction, relative to the view in FIG. 9.

The structure and function of the bracket 26e may be similar or identical to the structure and function of the bracket 26 described above, apart from any exceptions described below and/or shown in the figures. Accordingly, similar features will not be described again in detail. Like reference numerals are used hereinafter and in the drawings to identify like components, while like reference numerals containing letter extensions are used to identify those components that have been modified.

The bracket 26e may include a rod-receiving portion 244. The rod-receiving portion 244 may be coupled to, or otherwise integrally formed with, the bracket 26e. The rod-receiving portion 244 may be formed near the medial end 38e of the bracket 26e, and may include a seat portion 246, a first arm 248 and a second arm 250. The seat portion 246, the first arm 248, and the second arm 250 may define a rod-receiving aperture or channel 252. In the assembled configuration, the rod 24 may be disposed within the channel 252, such that the rod 24 engages the seat portion 246. The first arm 248 and the second arm 250 may include a threaded portion 260 for threadably mating with a set screw 264 or other suitable fastener. As will be explained in more detail below, in an assembled configuration, the set screw 264 can secure the rod 24 within the rod-receiving channel 252, such that the rod 24 extends from the sternal implant 22 in a substantially horizontal direction.

As illustrated, in the assembled configuration, the proximal end 110 of the support member 30 may be adjustably received within the third aperture 70 of a first bracket 26e, and the distal end 112 of the support member 30 may be adjustably received within the third aperture 70 of a second bracket 26e. A first rod 24 may be adjustably received within the rod-receiving channel 252 of the first bracket 26e and within one of the first apertures 140e of the sternal implant 22e. Similarly, a second rod 24 may be adjustably received within the rod-receiving channel 252 of the second bracket 26e and within another of the first apertures 140e of the sternal implant 22e. In this regard, the support member 30 may extend in a substantially vertical direction (relative to the view in FIG. 9), and the first and second rods 24 may extend in a substantially horizontal direction (relative to the view in FIG. 9). The rods 24 may be secured within the first apertures 140e using a set screw, a press fit configuration, or any other suitable technique.

A distance between the sternal implant 22e and the rod-receiving portion 244 of the bracket 26e, as measured along the third axis 143e, may be adjusted by changing the location of the sternal implant 22e relative to the sternum 16 and/or by changing the location of the bracket 26e relative to the rib 14. As the distance between the rod-receiving portion 244 and the sternal implant 22e is adjusted, the length of the rod 24 can be adjusted, such that the proximal end 150 of the rod 24 may be secured within the rod-receiving channel 252 of the bracket 26e, and the distal end 152 of the rod 24 may be secured within the first aperture 140e of the sternal implant 22e. In some configurations, the rod 24 can be trimmed or otherwise cut, such that the proximal end 150 of the rod 24 can be secured within the rod-receiving channel 252, and the distal end 152 of the rod 24 may be secured within the first aperture 140e. In this regard, it will also be appreciated that the rod 24 can translate, or otherwise be adjusted, within the second rod-receiving channel 252 in a direction substantially parallel to the third axis 143e, and/or translate, or otherwise be adjusted, within the first aperture 140e in a direction substantially parallel to the third axis 143e, such that the proximal end 150 of the rod 24 can be secured within the rod-receiving channel 252, and the distal end 152 of the rod 24 can be secured within the first aperture 140e. Similarly, the support member 30 can be slid or otherwise moved within the third aperture 70 of a first bracket 26e, such that a distance between brackets 26e, as measured along in a direction substantially perpendicular to the third axis 143e, can be adjusted. In this way, the rib reconstruction assembly 10e, including the flexible or bendable rod 24 and the adjustable support member 30, can allow a surgeon to effectively treat and repair variously-sized defects and abnormalities in the thoracic cavity 12, including defects in the radius of curvatures R1, R2 (i.e., horizontally extending defects and vertically extending defects).

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

What is claimed is:

1. An apparatus for the correction of chest deformities, the apparatus comprising:
   a rib implant for mounting to a rib, the rib implant including a first aperture having a first axis;
   a sternal implant for mounting to a sternum, the sternal implant including a second aperture having a second axis; and
   a first elongate member having a first end adjustably received in the first aperture and a second end adjustably received in the second aperture, wherein the first elongate member is configured to be adjustable in an axial direction relative to the first aperture of the rib implant or the second aperture of the sternal implant.

2. The apparatus of claim 1, wherein the first axis is generally parallel to the second axis.

3. The apparatus of claim 1, wherein the first axis is generally aligned with the second axis.

4. The apparatus of claim 3, wherein the rib implant includes a third aperture having a third axis, and wherein the rib is adjustably received in the third aperture.

5. The apparatus of claim 4, wherein the third axis intersects the first axis.

6. The apparatus of claim 4, wherein the third axis is generally parallel to the first axis.

7. The apparatus of claim 1, wherein the rib implant includes a first channel configured to receive a first rib, the first channel including a third axis intersecting the second axis.

8. The apparatus of claim 7, further comprising a suture member operatively securing the first rib within the first channel.

9. The apparatus of claim 1, further comprising a plate member for clamping the rib between the plate member and the rib implant.

10. The apparatus of claim 1, further comprising:
    a second rib implant for mounting to a rib, the second rib implant including a third aperture having a third axis, and wherein the sternal implant includes a fourth aperture having a fourth axis; and
    a second elongate member having a first end adjustably received in the third aperture and a second end adjustably received in the fourth aperture.

11. The apparatus of claim 10, wherein the third and fourth axes are generally parallel to the first and second axes.

12. The apparatus of claim 10, wherein the first rib implant includes a fifth aperture having a fifth axis, and the second rib implant includes a sixth aperture having a sixth axis.

13. The apparatus of claim 12, wherein the fifth axis is generally parallel to the sixth axis and generally perpendicular to the third and fourth axis.

14. The apparatus of claim 13, further comprising a support member disposed in the fifth and sixth apertures.

15. The apparatus of claim 1, wherein the first elongate member is flexible.

16. An apparatus for the correction of chest deformities, the apparatus comprising:
    a first bracket for mounting to a first rib, the first bracket including a first rib-receiving aperture, a first rod-receiving aperture, and a first support member-receiving aperture, the first rib-receiving aperture having a first rib-receiving axis, the first rod-receiving aperture having a first rod-receiving axis generally perpendicular to the first rib-receiving axis, and the first support member-receiving aperture having a first support member-receiving aperture axis generally parallel to the first rod-receiving axis;
    a second bracket for mounting to a second rib, the second bracket including a second rib-receiving aperture, a second rod-receiving aperture, and a second support member-receiving aperture, the second rib-receiving aperture having a second rib-receiving axis, the second rod-receiving aperture having a second rod-receiving axis generally perpendicular to the second rib-receiving axis, and the second support member-receiving aperture having a second support member-receiving aperture axis generally parallel to the second rod-receiving axis;
    a plate having first and second channels formed therein, the plate operable to clamp the first rib in the first channel and in the first rib-receiving aperture, and clamp the second rib in the second channel and in the second rib-receiving aperture;
    a sternal implant for mounting to a sternum, the sternal pt including a third rod-receiving aperture having a third rod-receiving axis;
    a support member adjustably disposed in the first and second support member-receiving apertures; and
    a flexible rod adjustably disposed in the first, second and third rod-receiving apertures.

17. The apparatus of claim 16, wherein the first rod-receiving axis is generally parallel to the third rod-receiving axis.

18. The apparatus of claim 16, wherein the first rib is adjustably received in the first rib-receiving aperture.

19. The apparatus of claim 16, further comprising a suture member operatively securing the sternum to the sternal implant.

20. An apparatus for the correction of chest deformities, the apparatus comprising:
    a rib implant for mounting to a rib, the rib implant including a rib-receiving aperture having a rib-receiving axis, a first rod-receiving aperture having a first rod-receiving axis, and a support member-receiving aperture having a support member-receiving axis extending in a direction substantially perpendicular to the rib-receiving axis and the first rod-receiving axis;
    a sternal implant for mounting to a sternum, the sternal implant including a second rod-receiving aperture having a second rod-receiving axis extending in a direction substantially parallel to the rib-receiving axis and the first rod-receiving axis; and
    a rod member having a first end adjustably disposed in the first rod-receiving aperture and a second end adjustably disposed in the second rod receiving aperture.

UNITED STATES PATENT AND TRADEMARK OFFICE
CERTIFICATE OF CORRECTION

PATENT NO. : 10,687,875 B2
APPLICATION NO. : 15/548174
DATED : June 23, 2020
INVENTOR(S) : Smits et al.

Page 1 of 1

It is certified that error appears in the above-identified patent and that said Letters Patent is hereby corrected as shown below:

In the Claims

In Column 16, Lines 28-29, in Claim 16, delete "p t" and insert --implant-- therefor Signed and Sealed this
Twenty-second Day of September, 2020

Andrei Iancu
*Director of the United States Patent and Trademark Office*